United States Patent [19]

Treuner

[11] Patent Number: 4,959,470

[45] Date of Patent: Sep. 25, 1990

[54] 2-OXO-[[(SUBSTITUTED SULFONYL)-AMINO]CARBONYL]-AZETIDINES

[75] Inventor: Uwe D. Treuner, Etterzhausen, Fed. Rep. of Germany

[73] Assignee: E. R. Squibb & Sons, Inc., Princeton, N.J.

[21] Appl. No.: 232,972

[22] Filed: Aug. 17, 1988

[51] Int. Cl.$^5$ .................... A61K 31/64; C07D 401/14; C07D 417/14

[52] U.S. Cl. .................................. 540/363; 540/357; 540/360; 540/364; 546/296

[58] Field of Search ................ 540/357, 360, 363, 364

[56] References Cited

U.S. PATENT DOCUMENTS

| | | | |
|---|---|---|---|
| 4,587,047 | 5/1986 | Breuer, et al. | 540/355 |
| 4,670,553 | 6/1987 | Breuer, et al. | 540/363 |
| 4,743,685 | 5/1988 | Breuer, et al. | 540/363 |

FOREIGN PATENT DOCUMENTS 2181130  4/1987  United Kingdom .

OTHER PUBLICATIONS

American Society for Microbiology, Program and Abstracts of the Twenty-Fifth Interscience Conference on Antimicrobial Agents and Chemotherapy, 1985, pp. 158 and 159.
Squibb Chemical Abstracts, 99 17546 9f, 1983.
Abstract No. 846 from 1984 ICAAC meeting, "Antimicrobial Activities of 1-Carbacephen Compounds and their Structure-Activity Relationships", Mochida et al.

Primary Examiner—Mark L. Berch
Attorney, Agent, or Firm—Donald J. Barrack; Stephen Venetianer

[57] ABSTRACT

Compnds having the formula

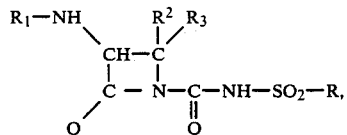

and pharmaceutically acceptable salts thereof, exhibit antibacterial activity wherein R is

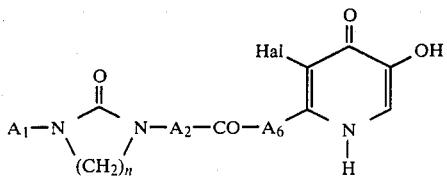

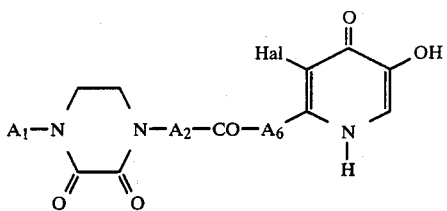

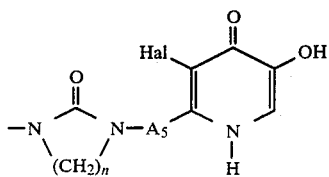

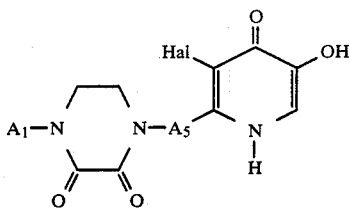

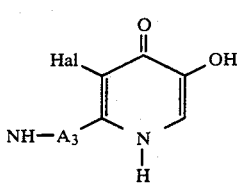

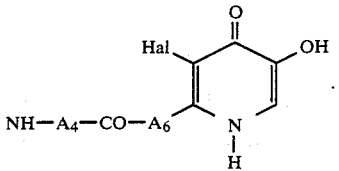

8 Claims, No Drawings

2-OXO-[[(SUBSTITUTED SULFONYL)-AMINO]CARBONYL]-AZETIDINES

BRIEF DESCRIPTION OF THE INVENTION

Compounds having the formula

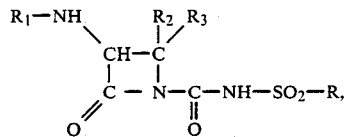

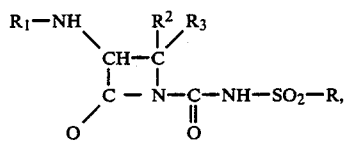

and pharmaceutically acceptable salts thereof, exhibit antibacterial activity. In formula I, and throughout the specification, the symbols are as defined below. R is

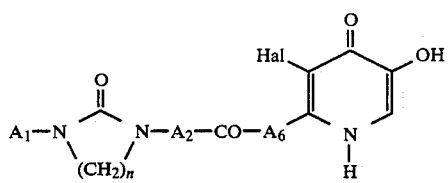

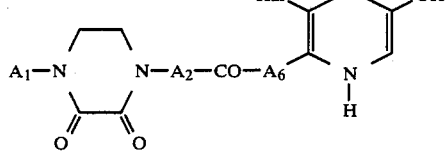

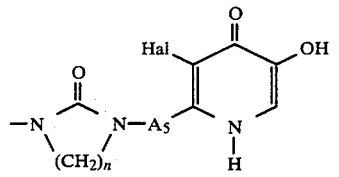

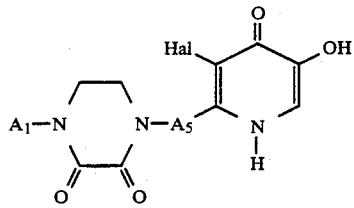

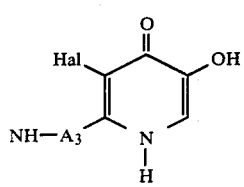

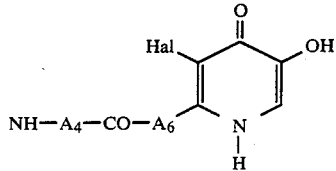

$R_1$ is an acyl group derived from a carboxylic acid;

$R_2$ and $R_3$ are the same or different and each is hydrogen, alkyl, alkenyl, alkynyl, cycloalkyl, phenyl, substituted phenyl or a 4, 5, 6 or 7-membered herterocycle (hereinafter referred to as $R_x$), or one of $R_2$ and $R_3$ is hydrogen and the other is azido, halomethyl, dihalomethyl, trihalomethyl, alkoxycarbonyl, 2-phenylethenyl, 2-phenylethynyl, carboxyl, —$CH_2X_1$ [wherein $X_1$ is azido, amino (—$NH_2$), hydroxy, carboxyl, alkoxycarbonyl, alkanoylamino, phenylcarbonylamino, (substituted phenyl)carbonylamino, alkylsulfonyloxy, phenylsulfonyloxy, (substituted phenyl)sulfonyloxy, phenyl, substituted phenyl, cyano,

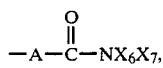

—S—$X_2$, or —O—$X_2$ (wherein A, $X_2$, $X_6$ and $X_7$ are as hereinafter defined)], —S—$X_2$ or —O—$X_2$ [wherein $X_2$ is alkyl, substituted alkyl, phenyl, substituted phenyl, phenylalkyl, (substituted pheny)alkyl, alkanoyl, substituted alkanoyl, phenylalkanoyl, (substituted phenyl)-alkanoyl, phenylcarbonyl, (substituted phenyl)-carbonyl, or heteroarylcarbonyl], and in the case of when $X_1$ is O—$X_2$ then $X_2$ can also be alkylideneamino, alkanoylamino, carboxyalkylideneamino, alkylsulphonylamino, alkoxycarbonyl alkylsulphonylamino or N,N-cyclodialkanoylamino,

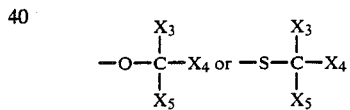

[wherein one of $X_3$ and $X_4$ is hydrogen and the other is hydrogen or alkyl, or $X_3$ and $X_4$ when taken together with the carbon atom to which they are attached form a cycloalkyl group; and $X_5$ is formyl, alkanoyl, phenylcarbonyl, (substituted phenyl)carbonyl, phenylalkylcarbonyl, (substituted phenyl)alkylcarbonyl, carboxyl, alkoxycarbonyl, aminocarbonyl

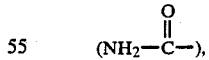

(substituted amino)carbonyl, or cyano (—C≡N)], or

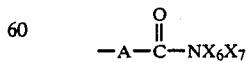

[wherein A is —CH=CH—, —$(CH_2)_m$—, —$(CH_2)_m$—O—, —$(CH_2)_m$—NH—, or —$CH_2$—S—$CH_2$—, m is 0, 1 or 2, and $X_6$ and $X_7$ are the same or different and each is hydrogen, alkyl, phenyl or substituted phenyl, or $X_6$ is hydrogen and $X_7$ is amino, substituted amino, alkanoylamino or alkoxy, or $X_6$ and $X_7$ when taken together with the nitrogen atom to which they are attached form a 4, 5, 6 or 7-membered heterocycle];

$$A_1 \text{ is a single bond, NH or NH—NH—}\overset{\overset{O}{\|}}{C};$$

$$A_2 \text{ is a single bond, NH, CH}_2\text{—CH}_2\text{—NH or }\overset{\overset{O}{\|}}{C}\text{NH—NH};$$

$$A_3 \text{ is a (CH}_2)_p\text{—; NH—CH}_2, \text{CH}_2\overset{\overset{O}{\|}}{C}\text{—NH—CH}_2, \text{OCH}_2;$$

$A_4$ is —NH n is two or three;
p is zero or one;
q is zero or one
t is one, two, three, or four
Hal is Br, Cl, or I
$A_5$ is a single bond; $CH_2$; NH—$CH_2$; —N=CH—; —CO—NH—$(CH_2)_q$
$A_6$ is a single bond; CH=CH; —$(CH_2)_t$—;

These groups are inserted in the structural formulas shown herein in the order in which they are presented (i.e., from left to right). For example, if R is

[structural formula with Hal, OH, $-A_1-N$, N—C, N-H groups] and $A_1$ is

HN—NH—$\overset{\overset{O}{\|}}{C}$—, the R group would be

[structural formula]

not —$\overset{\overset{O}{\|}}{C}$—HN—NH—N [structural formula]

Listed below are definitions of various terms used to describe the β-lactams of this invention. These definitions apply to the terms as they are used throughout the specification (unless they are otherwise limited in specific instances) either individually or as part of a larger group.

The terms "alkyl" and "alkoxy" refer to both straight and branched chain groups. Those groups having 1 to 10 carbon atoms are preferred.

The terms "cycloalkyl" and "cycloalkenyl" refer to cycloalkyl and cycloalkenyl groups having 3, 4, 5, 6 or 7 carbon atoms.

The term "substituted alkyl" refers to alkyl groups substituted with one or more (preferably 1, 2 or 3) azido, amino (—$NH_2$), halogen, hydroxy, carboxy, cyano, alkoxycarbonyl, aminocarbonyl, alkanoyloxy, alkoxy, phenyloxy, (substituted phenyl)oxy, mercapto, alkylthio, phenylthio, (substituted phenyl)thio, alkylsulfinyl, or alkylsulfonyl groups.

The terms "substituted alkanoyl refers to alkanoyl groups substituted with one or more (preferably 1, 2 or 3 azido, amino (—$NH_2$), halogen, hydroxy, carboxy, cyano, alkoxycarbonyl, aminocarbonyl, alkanoyloxy, alkoxy, phenyloxy, (substituted phenyl)oxy, mercapto, alkylthio, phenylthio, (substituted phenyl)thio, alkylsulfinyl, or alkylsulfonyl groups.

The terms "alkanoyl", "alkenyl", and "alkynyl" refer to both straight and branched chain groups. Those groups having 2 to 10 carbons atoms are preferred.

The terms "halogen" and "halo" refer to fluorine, chlorine, bromine and iodine.

The term "substituted phenyl" refers to a phenyl group substituted with 1, 2 or 3 amino (—$NH_2$), halogen, hydroxyl, trifluoromethyl, alkyl (of 1 to 4 carbon atoms), alkoxy (of 1 to 4 carbon atoms), alkanoyloxy, aminocarbonyl, or carboxy groups.

The expression "a 4, 5, 6 or 7-membered heterocycle" (referred to as "$R_x$") refers to substituted and unsubstituted, aromatic and non-aromatic groups containing one or more (preferably 1, 2 or 3) nitrogen, oxygen or sulfur atoms. Exemplary substituents are oxo (=O), halogen, hydroxy, nitro, amino, cyano, trifluoromethyl, alkyl of 1 to 4 carbons, alkoxy of 1 to 4 carbons, alkylsulfonyl, phenyl, substituted phenyl, 2-furfurylideneamino

[structural formula of furyl-CH=N—]

benzylideneamino and substituted alkyl groups (wherein the alkyl group has 1 to 4 carbons). One type of "4, 5, 6 or 7-membered heterocycle" is the "heteroaryl" group. The term "heteroaryl" refers to those 4, 5, 6 or 7-membered heterocycles which are aromatic. Exemplary heteroaryl groups are substituted and unsubstituted pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, and tetrazolyl. Exemplary nonaromatic heterocycles (i.e., fully or partially saturated heterocyclic groups) are substituted and unsubstituted azetidinyl, oxetanyl, thietanyl, piperidinyl, piperazinyl, imidazolidinyl, oxazolidinyl, pyrrolidinyl, tetrahydropyrimidinyl, dihydrothiazolyl and hexahydroazepinyl. Exemplary of the substituted 4, 5, 6 or 7-membered heterocycles are 1-alkyl-3-azetidinyl, 2-oxo-1-imidazolidinyl, 3-alkylsulfonyl-2-oxo-1-imidazolidinyl, 3-benzylideneamino-2-oxo-1-imidazolidinyl, 3-alkyl-2-oxo-1-imidazolidinyl, 3-phenyl (or substituted phenyl)-2-oxo-1-imidazolidinyl, 3-benzyl-2-oxo-1-imidazolidinyl, 3-(2-aminoethyl)-2-oxo-1-imidazolidinyl, 3-amino-2-oxo-1-imidazolidinyl, 3-[(alkoxycarbonyl)amino]-2-oxo-1-imidazolidinyl, 3-[2-[(alkoxycarbonyl)amino]ethyl]-2-oxo-1-imidazolidinyl, 2-oxo-1-pyrrolidinyl, 2-oxo-3-oxazolidinyl, 4-hydroxy-6-methyl-2-pyrimidinyl, 2-oxo-1-hexahydroazepinyl, 2-oxo-3-pyrrolidinyl, 2-oxo-3-tetrahydrofuranyl, 2,3-dioxo-1-piperazinyl, 2,5-dioxo-1-piperazinyl, 4-alkyl-2,3-dioxo-1-piperazinyl, and 4-phenyl-2,3-dioxo-1-piperazinyl.

The term "substituted amino" refers to a group having the formula —$NX_8X_9$ wherein $X_8$ is hydrogen, alkyl, phenyl, substituted phenyl, phenylalkyl or (substituted phenyl)alkyl, and $X_9$ is alkyl, phenyl, substituted phenyl, phenylalkyl, (substituted phenyl)alkyl, hydroxy, cyano, alkoxy, phenylalkoxy, or amino (—NH$_2$).

The term "acyl" refers to all organic radicals derived from an organic acid (i.e., a carboxylic acid) by removal of the hydroxyl group. Certain acyl groups are, of course, preferred but this preference should not be viewed as a limitation of the scope of this invention. Exemplary acyl groups are those acyl groups which have been used in the past to acylate β-lactam antibiotics including 6-aminopenicillanic acid and derivates and 7-aminocephalosporanic acid and derivatives; see, for example *Cephalosporins and Penicillins*, edited by Flynn, Academic Press (1972), German offenlegungsschrift 2,716,677, published Oct. 10, 1978, Belgian patent 867,994, published Dec. 11, 1978, U.S. Pat. No. 4,152,432, issued May 1, 1979, U.S. Pat. No. 4,172,199, issued Oct. 23, 1979, and British patent 1,348,894, published Mar. 27, 1974. The portions of these references describing various acyl groups re incorporated herein by reference. The following list of acyl groups is presented to further exemplify the term "acyl"; it should not be regarded as limiting that term. Exemplary acyl groups are:

(a) Aliphatic groups having the formula

wherein $R_a$ is alkyl; cycloalkyl; alkoxy; alkenyl; cycloalkenyl; cyclohexadienyl; or alkyl or alkenyl substituted with one or more halogen, cyano, nitro, amino, mercapto, alkylthio, or cyanomethyltheio groups.

(b) Carbocyclic aromatic groups having the formula

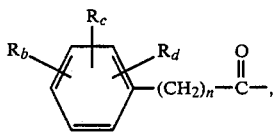

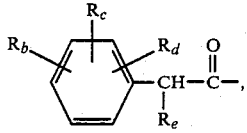

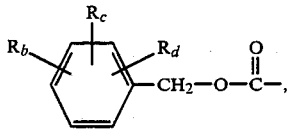

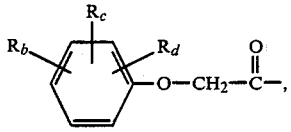

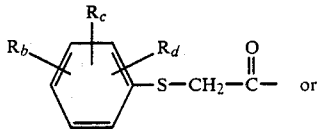 or

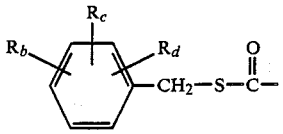

wherein n is 0, 1, 2 or 3; $R_b$, $R_c$, and $R_d$ each is independently hydrogen, halogen, hydroxyl, nitro, amino, cyano, trifluoromethyl, alkyl of 1 to 4 carbon atoms, alkoxy of 1 to 4 carbon atoms or aminomethyl; and $R_e$ is amino, hydroxyl, a carboxyl salt, protected carboxyl, formyloxy, a sulfo salt, a sulfoamino salt, azido, halogen, hydrazino, alkylhydrazino, phenylhydrazino, or [(alkylthio)thioxomethyl]thio.

Preferred carbocyclic aromatic acyl groups include those having the formula

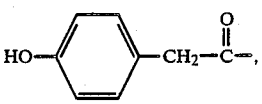

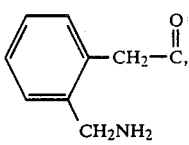

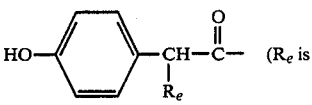 ($R_e$ is preferably a carboxyl salt or sulfo salt) and

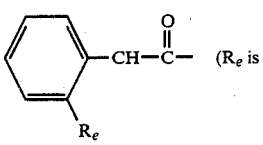 ($R_e$ is preferably a carboxyl salt or sulfo salt).

(c) Heteroaromatic groups having the formula

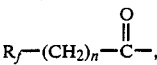

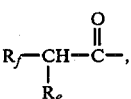

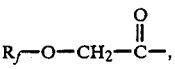

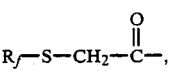

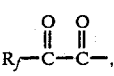

wherein n is 0, 1, 2 or 3; $R_e$ is as defined above; and $R_f$ is a substituted or unsubstituted 5-, 6- or 7-membered heterocyclic ring containing 1, 2, 3 or 4 (preferably 1 or 2) nitrogen, oxygen and sulfur atoms. Exemplary heterocyclic rings are thienyl, furyl, pyrrolyl, pyridinyl, pyrazolyl, pyrazinyl, thiazolyl, pyrimidinyl, thiadiazolyl and tetrazolyl. Examplary substituents are halogen, hydroxyl, nitro, amino, protected amino, cyano, trifluoromethyl, alkyl of 1 to 4 carbon atoms, alkoxy of 1 to 4 carbon atoms, or

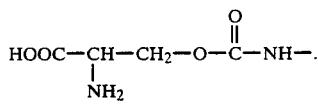

Preferred heteroaromatic acyl groups include those groups of the above formulas wherein $R_f$ is 2-amino-4-thiazolyl, 2-amino-5-halo-4-thiazolyl, 4-aminopyrimidin-2-yl, 5-amino-1,2,4-thiadiazol-3-yl, 2-thienyl, 2-furanyl, or 6-aminopyridin-2-yl.

(d) [[(4-Substituted-2,3-dioxo-1-piperazinyl)carbonyl]amino]arylacetyl groups having the formula

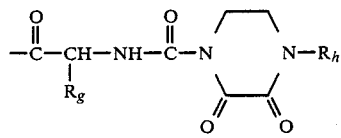

wherein $R_g$ is an aromatic group (including carbocyclic aromatics such as those of the formula

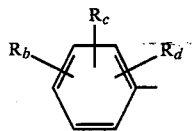

and heteroaromatics as included within the definition of $R_f$); and $R_h$ is alkyl, substituted alkyl (wherein the alkyl group is substituted with one or more halogen, cyano, nitro, amino or mercapto groups), arylmethyleneamino (i.e., $-NH=CH-R_g$ wherein $R_g$ is as defined above), arylcarbonylamino

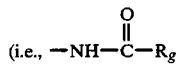

(i.e.,
wherein $R_g$ is as defined above) or alkylcarbonylamino.

Preferred [[(4-substituted-2,3-dioxo-1-piperazinyl)carbonyl]amino]arylacetyl groups include those wherein $R_h$ is ethyl, phenylmethyleneamino or 2-furylmethyleneamino.

(e) (Substituted oximino)arylacetyl groups having the formula

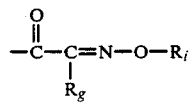

wherein $R_g$ is as defined above and $R_i$ is hydrogen, alkyl, cycloalkyl,

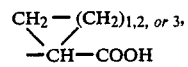

2-pyrazolylmethyl, (2-oxo-3-pyrrolidinyl)methyl, alkylaminocarbonyl, arylaminocarbonyl

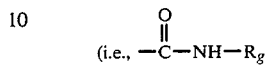

(i.e., $-C-NH-R_g$ is as defined above) or substituted with one or more halogen, cyano, nitro, amino, mercapto, alkylthio, aromatic group (as defined by $R_g$), carboxyl (including salts thereof), amido, alkoxycarbonyl, phenylmethoxycarbonyl, diphenylmethoxycarbonyl, phenylmethoxycarbonyl, dihydroxyphosphinyl, hydroxy(phenylmethoxy)phosphinyl, dialkoxyphosphinyl or tetrazolyl substituents).

Preferred (substituted oxyimino) arylacetyl groups include those wherein $R_g$ is 2-amino-4-thiazolyl. Also preferred are those groups wherein $R_i$ is methyl, ethyl, carboxymethyl, 1-carboxy-1-ethyl (R and S isomer) 1-carboxy-1-methylethyl, 2,2,2-trifluoroethyl or 1-carboxycyclopropyl, 1-carboxycyclobutyl or 1-carboxycyclopentyl.

(f) (Acylamino)arylacetyl groups having the formula

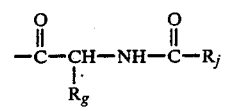

wherein $R_g$ is as defined above and $R_j$ is

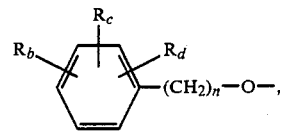

amino, alkylamino, (cyanoalkyl)-amino, amido, alkylamido, (cyanoalkyl)amido,

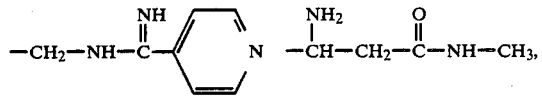

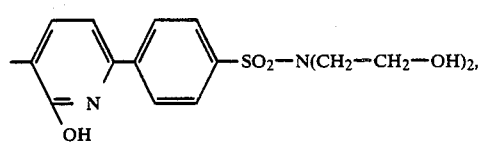

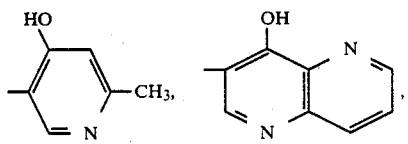

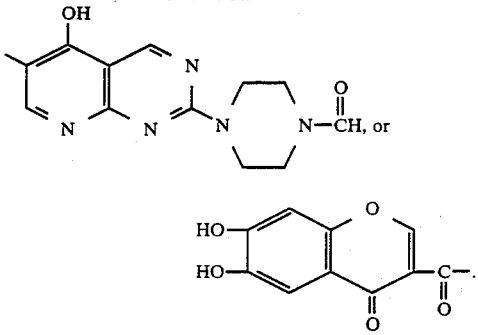

Preferred (acylamino)arylacetyl groups of the above formula include those groups wherein $R_j$ is amino or amido. Also preferred are those groups wherein $R_g$ is phenyl or 2-thienyl.

(g) [[[3-Substituted-2-oxo-1-imidazolidinyl]carbonyl]amino]arylacetyl groups having the formula

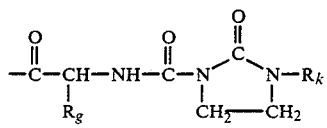

wherein $R_g$ is as defined above and $R_k$ is hydrogen, alkylsulfonyl, arylmethyleneamino (i.e., $-N=CH-R_g$ wherein $R_g$ is as defined above),

(wherein $R_m$ is hydrogen, alkyl or halogen substituted alkyl), aromatic group (as defined by $R_g$ above), alkyl or substituted alkyl (wherein the alkyl group is substituted with one or more halogen, cyano, nitro, amino or mercapto groups).

Preferred [[[3-substituted-2-oxo-1-imidazolidinyl]carbonyl]amino]arylacetyl groups of the above formula include those wherein $R_g$ is phenyl or 2-thienyl. Also preferred are those groups wherein $R_k$ is hydrogen, methylsulfonyl, phenylmethyleneamino or 2-furylmethyleneamino.

The compounds of this invention form basic salts with various inorganic and organic bases which are also within the scope of this invention. Such salts include ammonium salts, alkali metal salts, alkaline earth metal salts, salts with organic bases, e.g., dicyclohexylamine, benzathine, N-methyl-D-glucamine, hydrabamine and the like. The pharmaceutically acceptable salts are preferred, although other salts are also useful, e.g., in isolating or purifying the product.

Some of the compounds of this invention may be crystallized or recrystallized from solvents containing water. In these cases, water of hydration may be formed. This invention contemplates stoichiometric hydrates as well as compounds containing variable amounts of water that may be produced by processes such as lyophilization.

The β-lactams of formula I contain at least one chiral center—the carbon atom in the 3-position of the β-lactam nucleus to which the acylamino substituent ("$R_1$—NH—") is attached. This invention is directed to those β-lactams which have been described above, wherein the stereochemistry at the chiral center in the 3-position of the β-lactam nucleus is the same as the configuration at the carbon atom in the 6-position of naturally occurring penicillins (e.g., penicillin G) and as the configuration at the carbon atom in the 7-position of naturally occurring cephalosporins (e.g., cephalosporin C). Also included within the scope of this invention are racemic mixtures which contain the above-described β-lactams.

It is understood that all hydroxypyridone compounds of this invention may exist as their dihydroxypyridine tautomers.

DETAILED DESCRIPTION OF THE INVENTION

The β-lactams of formula I, and pharmaceutically acceptable salts thereof, have activity against gram-positive and gram-negative organisms. The compounds of this invention can be used as agents to combat bacterial infections (including urinary tract infections and respiratory infections) in mammalian species, such as domesticated animals (e.g., dogs, cats, cows, horses, and the like) and humans.

For combating bacterial infections in mammals, a compound of this invention can be administered to a mammal in need thereof in an amount of about 1.4 mg/kg/day to about 350 mg/kg/day, preferably about 14 mg/kg/day to about 100 mg/kg/day. All modes of administration which have been used in the past to deliver penicillins and cephalosporins to the site of the infection are also contemplated for use with β-lactams of this invention. Such methods of administration include oral, intravenous, intramuscular, and as a suppository.

The β-lactams of formula I can be prepared from a 3-protected amino-2-azetidinone having the formula

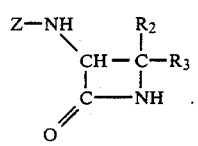

In formula II, and throughout the specification, the symbol "Z" refers to an amino protecting group. These groups are well known in the field of β-lactam chemistry, and the particular group chosen is not critical. Benzyloxycarbonyl, trityl, and t-butoxycarbonyl are exemplary protecting groups. The reaction of a β-lactam of formula II with an isocyanate having the formula $$O=C=N-SO_2-L,\qquad\text{(III)}$$

wherein L is a leaving group such as chlorine, yields the corresponding compound having the formula

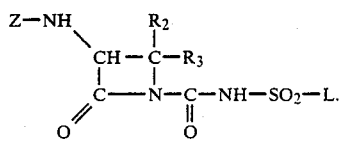

The reaction is preferably run in an inert organic solvent, e.g., ethyl acetate, tetrahydrofuran, dimethoxyethane, dichloromethane, acetonitrile or mixtures of these solvents. Displacement of the leaving group "L" with the desired group "R" can be accomplished using the appropriate nucleophile having the formula $$RH, \qquad (V)$$

optionally in the presence of a base (e.g., triethylamine), and yields the corresponding compound having the formula

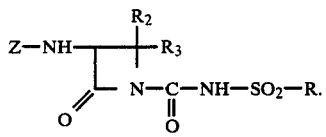
VI

Alternaively, the displacement of the leaving group can be accomplished by reaction of a compound of formula IV with a protected form of a compound of formula V. Following the displacement reaction, the protecting groups can be removed using art-recognized techniques to yield a compound of formula VI.

Protected forms of a compound of formula V, and of all reactants described herein which contain a 3-hydroxy-4-pyridone moiety, include those compounds wherein the hydroxyl group is protected, those compounds wherein the hydroxyl group and the ring nitrogen are protected, and those compounds wherein both pyridone oxygens are protected. Exemplary protecting groups are silyl (e.g., trimethylsilyl), benzyl and acyl (e.g., acetyl). If silyl is used, later deprotection can be accomplished using hydrolysis or fluoride mediated cleavage. If benzyl is used, later deprotection can be accomplished by hydrogenolysis or treatment with trifluoroacetic acid/thioanisole. If acyl is used, later deprotection can be accomplished by hydrolysis.

Deprotection of a compound of formula VI using conventional techniques yields the corresponding key intermediate having the formula

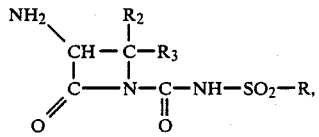
VII or a salt thereof. The particular deprotection reaction used will, of course, depend on the protecting group ("Z") present. If, for example, Z is a t-butoxycarbonyl protecting group, deprotection can be accomplished by treatment of a compound of formula VI with acid (e.g., formic acid or trifluoroacetic acid). If, for example, Z is a benzyloxycarbonyl protecting group, deprotection can be accomplished by catalytic hydrogenation of a compound of formula VI. Alternatively, the Z protecting group can be removed simultaneously with the other pyridone protecting groups immediately following the above-described displacement reaction.

Well known acylation techniques can be used to convert an intermediate of formula VII to a corresponding product of formula I. Exemplary techniques include reaction of a compound of formula VII with a carboxylic acid ($R_1$—OH), or corresponding carboxylic acid halide or carboxylic acid anhydride. The reaction with a carboxylic acid proceeds most readily in the presence of a carbodiimide such as dicyclohexylcarbodiimide and a substance capable of forming an active ester in situ such as N-hydroxybenzotriazole. In those instances where the acyl group ($R_1$) contains reactive functionality (such as amino or carboxyl groups) it may be necessary to first protect those functional groups, then carry out the acylation reaction, and finally deprotect the resulting product.

An alternative procedure for preparing the compounds of formula I comprises first acylating (acylation techniques have been described above) a 3-amino-2-azetidinone having the formula

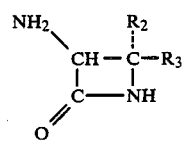
VIII to yield an intermediate having the formula

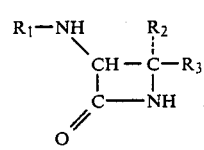
IX

A

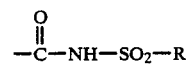

activating group can be introduced in the 1-position of a compound of formula IX (using the procedures described above) to obtain the corresponding product of formula I. In those instances wherein the acyl side-chain "$R_1$" contains reactive functionality (such as amino groups), it may be necessary to first protect those functional groups, then carry out the addition of the activating group in the 1-position, and finally deprotect the resulting product.

Still another synthesis for the preparation of compounds of formula I comprises the use of a 3-azido-2-azetidinone having the formula

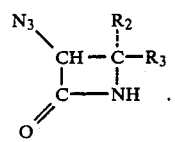
X

A

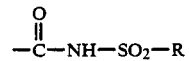

activating group can be introduced in the 1-position of a compound of formula X (using the procedures described above) to obtain the corresponding compound having the formula

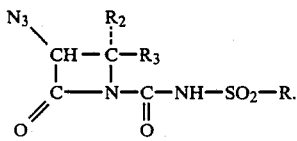

Reduction of an intermediate of formula XI yields the corresponding intermediate having the formula

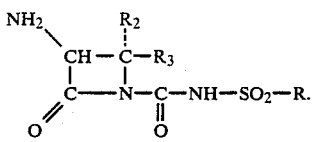

The reduction can be accomplished by catalytic (e.g., palladium on charcoal or platinum oxide) hydrogenation or with reducing agents such as zinc or triphenylphosphine. As described above, from these key intermediates (compounds of formula VII), using conventional acylation techniques, it is possible to prepare the products of formula I.

Alternatively, a 3-azido-2-azetidinone of formula X can be reduced to the corresponding 3-amino-2-azetidinone having the formula

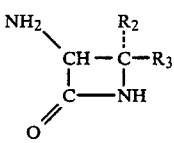

The reduction can be accomplished by catalytic (e.g., palladium on charcoal or platinum oxide) hydrogenation or with reducing agents such as zinc or triphenylphosphine. A 3-amino-2-azetidinone of formula VIII can be reacted as described above (i.e., first acylated and then treated as described above to introduce a

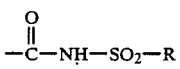

activating group in the 1-position) to yield the products of formula I.

Still another synthesis for preparing the compounds of formula I wherein $R_2$ and $R_3$ are each hydrogen utilizes a 6-acylaminopenicillanic acid having the formula

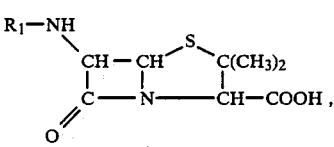

or a salt thereof, as the starting material. By adapting procedures described in the literature, 3-acylamino-2-azetidinone can be obtained from the corresponding 6-acylaminopenicillanic acid of formula XII: see, for example *Chem. Soc. Special Publication* No. 28, pg. 288 (1977), *The Chemistry of Penicillins*, Princeton University Press, pg. 257, and *Synthesis*, 494 (1977).

As described in the literature 6-acylaminopenicillanic acid, or a salt thereof, can be desulfurized to yield a compound having the formula

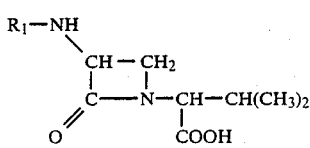

by reduction using Raney nickel. The reaction can be run in water under reflux conditions.

Replacement of the carboxyl group of a compound of formula XIII with an acetate group followed by hydrolysis yields the corresponding 3-acylamino-2-azetidinone having the formula

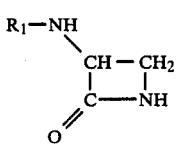

Treatment of a compound of formula XIII with cupric acetate and lead tetraacetate in an organic solvent (e.g., acetonitrile) replaces the carboxyl group with an acetate group. Hydrolysis of the resulting compound can be accomplished using potassium carbonate in the presence of sodium borohydride.

A

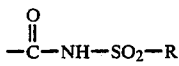

activating group can be introduced in the 1-position of a compound of formula XIV (yielding products of formula I wherein $R_2$ and $R_3$ are each hydrogen) using the procedures described above.

Still another variation of the above-described synthetic routes for preparing a compound of formula I wherein $R_2$ and $R_3$ are each hydrogen comprises first desulfurizing 6-aminopenicillanic acid, acylating the resulting compound to yield a compound of formula XIII and then proceeding as described above to obtain first a 3-acylamino-2-azetidinone of formula XIV and then a product of formula I.

The azetidinones of formula I can also be prepared from amino acids having the formula

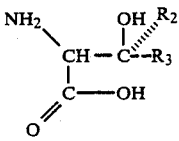

The amino group is first protected (with a protecting group "Z", e.g., t-butoxycarbonyl). The carboxyl group of the protected amino acid is then reacted with an amine having the formula

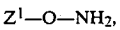

wherein $Z^1$ is alkyl, benzyl or triphenylmethyl, in the presence of a carbodiimide to yield a compound having the formula

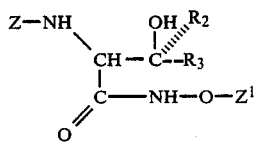

XVII

The hydroxyl group of a compound of the formula XVII is converted to a leaving group ("OL) with a reagent, such as methanesulfonyl chloride or pyridine-SO₃ complex.

The fully protected compound having the formula

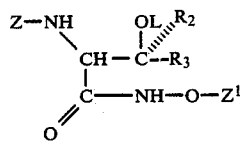

XVIII is cyclized by treatment with base, e.g., potassium carbonate. The reaction is preferably carried out in an organic solvent or an organic solvent/water mixture under reflux conditions, and yields a compound having the formula

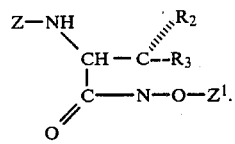

XIX

Alternatively, cyclization of a compound of formula XVII can be accomplished without first converting the hydroxyl group to a leaving group. Treatment of a compound of formula XVII with triphenylphosphine and diethylazodiacarboxylate, yields a compound of formula XIX.

Exemplary procedures for the conversion of a compound of formula XVIII to a compound of formula XIX are described in *J. Amer. Chem. Soc.*, 102, 7026 (1980) and *J. Org. Chem.*, 47, 5160 (1982).

Both of the methods disclosed above for ring closure of a compound of formula XVII result in the inversion of the sterochemistry at the carbon atom bearing the R₂ and R₃ substituents when R₂ and R₃ is not the same.

Removal of the protecting group from the 1-position of an azetidinone of formula XIX can be accomplished via sodium reaction when Z¹ is alkyl, and yields an intermediate having the formula

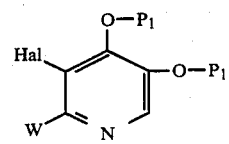

II (at least one of R₂ and R₃ is hydrogen). If Z¹ is benzyl, catalytic (e.g., palladium on charcoal) hydrogenation will initially yield the corresponding N-hydroxy compound, which upon treatment with titanium trichloride yields an intermediate of formula II. If Z¹ is triphenylmethyl, formic acid or 70% acetic acid/water will initially yield the corresponding N-hydroxy compound.

A

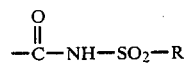

activating group can be introduced in the 1-position of a compound of formula II using the procedures described above, and the resulting compound can be deprotected and acylated.

The nucleophiles RH of formula V can be prepared in a similar manner as described in U.S. Ser. No. 907,441 filed Sept. 15, 1986.

Alternatively, the compounds of formula I can be formed by reacting a compound having the formula

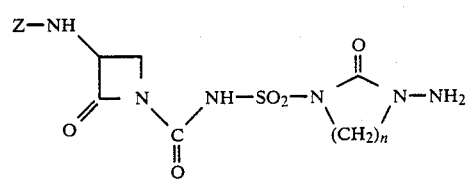

XX with a compound of the formula

XXI wherein P₁ is hydrogen or a hydroxyl protecting group such as benzyl, alkoxylcarbonyl, alkanoyl, phenyl carbonyl or substituted phenyl carbonyl and W is COOH, —CH=CH—COOH or $$-\overset{O}{\underset{\|}{C}}-H$$

to yield intermediates having the formula

XXII wherein T is $$-\overset{H}{\underset{|}{N}}-\overset{O}{\underset{\|}{C}}-, \quad -\overset{H}{\underset{|}{N}}-\overset{O}{\underset{\|}{C}}-CH=CH-,$$

or —N=CH—.

Intermediate compound XXII can be fully deprotected in one step by conventional methods to yield intermediates of the formula

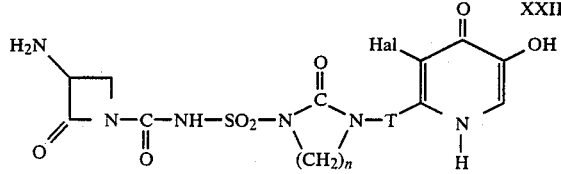 XXIII or a salt thereof. Acrylation with a compound of the formula

—OH    (XXIV)

or activated derivatives thereof will yield compounds of formula I.

It is also possible to synthesize the compounds of formula I by reacting compounds of the formula

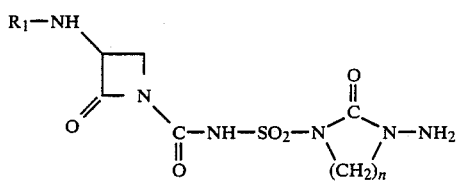 XXV with compounds of the formula

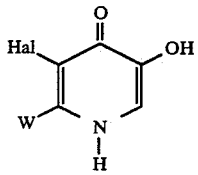 XXVI wherein W is —COOH, —CH=CH—COOH or

by conventional coupling methods. The above described methods involving the compounds of formula XX or XXV are also applicable by substituting the compounds represented by the formula

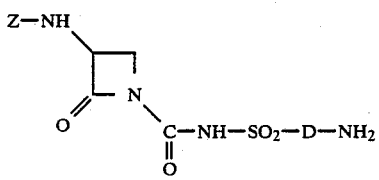 XXVII wherein D is NH,

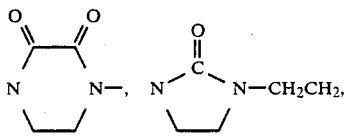

or

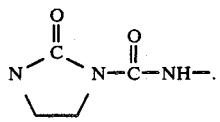

Compounds of formula XX and XXV can be prepared by reacting a compound of formula IV or a compound of formula IV when Z equals $R_1$ in a solvent, such as methylene chloride, tetrahydrofuran, acetonitrile or ethyl acetate, with compounds of the formula

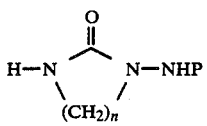

and subsequent deprotection of P. P is an amino protecting group such as tert-butyloxycarbonyl or benzyloxycarbonyl.

Compounds of formula XXVII can be prepared in a manner similar to the preparation of compounds of the formulae XX and XXV.

This invention includes the novel hydroxypyridones or the deprotected hydroxypyridones represented by the formulas

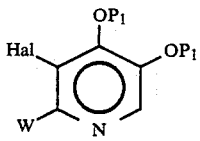 XXI

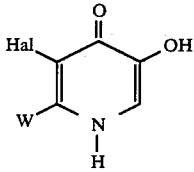 XXVI wherein W is COOH, —HC=CH—COOH or

Compounds of XXI may be converted to compounds of formula XXVI when $P_1$ is a protecting group using standard methods known in the art. These novel hydroxypyridones are used to synthesize the nucleophile RH or reacted with compounds of formula XX and XXV Compounds XXVI and XXI are prepared by reacting a compound of the formula

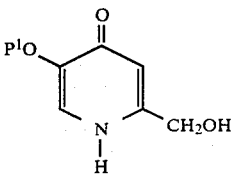 XXIX with bromine at room temperature suspended in acetic acid and sodium acetate to yield a compound of the formula

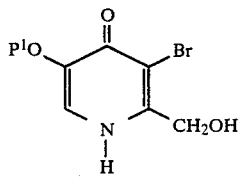 XXX

The corresponding pyridinecarboxylic acid is made from a compound of the formula XXXI

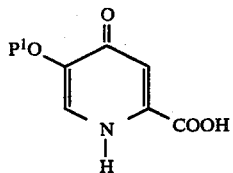

using the above bromination method.

Compound XXX can be converted to the corresponding alkyl halide of the formula XXXII by reacting with chlorinating agents such as $SOCl_2$ in solvents such as tetrahydrofuran; $CH_2Cl_2$ or $CHCl_3$ at room temperature or with slight heating.

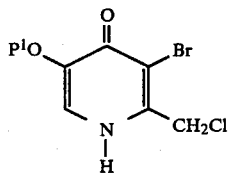 XXXII

Compound XXXII can be converted to the corresponding alkylamino compound of the formula XXXIII by conventional methods for $CH_2-X \rightarrow -CH_2-NH_2$ transformations (e.g. via the $-CH_2N_3$ (azidomethyl) intermediate and its reduction to XXXII by hydrogenation or with $H_2S$ TEA treatment.

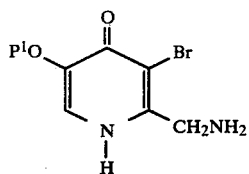 XXXIII or to the compound having the formula XXXIV by reaction with suitable N-protected hydroxyl amino derivatives such as HO—NH—BOC or

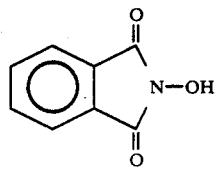

and a base and deprotection of the formed intermediates.

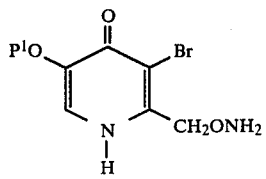 XXXIV

Compound XXX can be reacted with $MnO_2$ to yield a compound of the formula

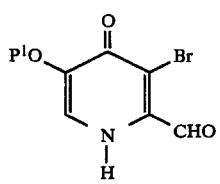 XXXV

Compound XXXV can be subjected to a Wittig or Horner reaction to yield a compound of the formula

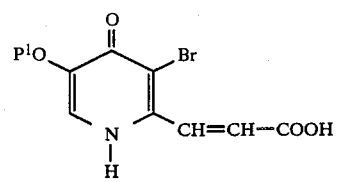 XXXVI

Compound XXXV can also be prepared by reacting a compound of the formula XXXVII (a stable half acetate of compound XXXV)

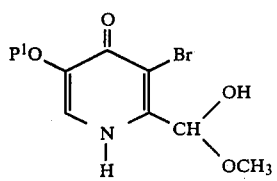 XXXVII with bromine in acetic acid.

The following examples are specific embodiments of this invention.

EXAMPLE 1

3-Bromo-1,4-dihydro-4-oxo-5-(phenylmethoxy)-2-pyridinecarboxylic acid

To 24.32 g comenamic acid suspended in 1000 ml of acetic acid, and 8.3 g sodium acetate, were added 20 g $Br_2$ dropwise at room temperature with stirring. After two hours a yellow solution was formed. The acetic acid was then distilled off and the residue stirred with 300 ml ice water. The precipitate formed was filtered off and washed with 50 ml ice water. The precipitate was dissolved in 150 ml water by adding $Na_2CO_3$ until a clear solution was obtained. Then pH was adjusted to pH 2 with hydrochloric acid. White crystals of the title compound were formed. After filtration and washing with water and isopropanol, the title compound was dried over $P_2O_5$ in vacuo. Yield: 29.5 g, M.P. 120° C.

EXAMPLE 2

3-Bromo-1,4-dihydro-4-oxo-N-(2-oxo-1-imidazolidinyl)-5-(phenylmethoxy)-2-pyridinecarboxamide 3.24 g of 3-bromo5-(0-phenylmethyl) comenanic acid, 0.75 g of N-hydroxybenzotriazole and 2.06 g dicylohexylcarbodiimide were dissolved in 100 ml DMF and stirred at room temperature for 1 hour. 1.02 g N-amino-2-imidazolidinone were added and stirring continued for 12 hours. The formed dicyclohexylurea was filtered off. The filtrate solvent was distilled off and the residue recrystallized from dioxane. White crystals (3.82 g) of the title compound were obtained.

EXAMPLE 3

3-Bromo-1,4-dihydro-4-oxo-5-(phenylmethoxy)-2-pyridinecarboxylic acid, 2-[(1,1-dimethyl-ethoxy)carbonyl]hydrazide 3.24 g of 3-bromo-5-(0-phenylmethyl) comenamic acid, 1.5 g N-hydroxy benzotriazole and 2.06 g dicylohexylcarbodiimide were dissolved in 50 ml DMF and stirred for 1 hour at room temperature. 1.33 g of t.-butoxycarbonylhydrazide were then added and stirring continued overnight. The formed dicyclohexylurea was filtered off and the filtrate solvent distilled off. The residue was stirred with 50 ml of ice water. The title compound was isolated by filtration and recrystallized from dioxane/water.

3.87 g white crystals were yielded. M.P.=128° C. (dec.)

EXAMPLE 4

3-Bromo-1,4-dihydro-4-oxo-5-(phenylmethoxy)-2-pyridinecarboxylic acid, hydrazide 2.19 g of the title compound of Example 3 were stirred at 0° C. for 30 minutes in 20 ml trifluoroacetic acid. 100 ml diethylether were then added and the precipitated of the trifluoroacetic acid salt of the title compound was isolated by filtration and dissolved in 30 ml water. The pH was then adjusted to 7.0. The title compound was obtained by precipitation and filtration as a beige precipitate, yield: 1.34 g.
M.P.=184° C.

EXAMPLE 5

(S)-1-[[[[3-Bromo-1,4-dihydro-4-oxo-5-(phenylmethoxy)-2-pyridinyl]carbonyl]amino]-2-oxo-1-imidazolidinyl]sulfonyl]amino]carbonyl]-2-oxo-3-azetidinyl]carbamic acid, phenylmethyl ester Solution A 1.99 g benzyloxycarbonyl-azetidinon and 1.29 g chlorosulfonyl isocyanate were stirred for 1 hour in 50 ml ethylacetate at 5° C. A solution of (S)-[1-[[chlorosulfonyl)amino]carbonyl]-2-oxo-3-azetidinyl]-carbamic acid, phenylmethyl ester was obtained.

Solution B 3.6 g of the title compound of Example 2 and 5.5 g N-methyl-trimethylsilyltrifluoroacetamide was stirred in 100 ml ethylacetate for 1 hour. A clear solution was formed (Solution B). Solution A was then added dropwise to solution B at 0° C. and stirred overnight. The solvent was then distilled off and the residue stirred with 100 ml isopropanol for 1 hour. A white precipitate of crude title compound, H. I. 53%, was obtained. This was suspended in 30 ml ice water and the pH was adjusted to 6 with NaHCO$_3$. After filtration, the filtrate was chromatographed on silica gel, water as eluent. Fr. 200-286 contained 1.3 g sodium salt of title compound H.I. 73.4%. After two additional column chromatographies 0.21 g title compound sodium salt, H.K. 84% were obtained. This was dissolved in water and the pH was adjusted to 2 with 2NHCl. A white precipitate of title compound was obtained, 0.11 g.

EXAMPLE 6 AND EXAMPLE 7

3-Bromo-4,5-bis(phenylmethoxy)-2-pyridinecarboxylic acid, phenylmethyl ester 12.96 g of the title compound of Example 1, 5.52 g of potassium carbonate and 10.40 g benzylbromide was dissolved in 200 ml DMF and kept at 80°-90° C. for 18 hours. The solvent was then distilled off in vacuo and the oil residue dissolved in 100 ml ethyl acetate and 100 ml water. The organic layer was separated and washed again with 50 ml water. The solvent of the dried organic phase was then stripped off to afford an oily residue (18 g). The oil was dissolved in 30 ml ethyl acetate/cyclohexane (1:1). 4.1 g 3-bromo-1,4-dihydro-4-oxo-5-(phenylmethoxy)-1-(phenylmethyl)-2-pyridinecarboxylic acid, phenylmethyl ester crystallized from the solution. The filtrate was chromatographed on silica gel using ethylacetate/cyclohexane (1:1) as eluent. Fractions 33-35 contained 4 g pure title compound M.P.=98°-100° C.; another 1.9 title compound with 10% 3-Bromo-1,4-dihydro-4-oxo-5-(phenylmethoxy)-1-(phenylmethyl)-2-pyridinecarboxylic acid, phenylmethyl ester were obtained from fractions 57-104.
M.P.=120° C.

EXAMPLE 8

3-Bromo-4,5-bis(phenylmethoxy)-2-pyridinecarboxylic acid 3.8 g of 3-Bromo-1,4-dihydro-4-oxo-5-(phenylmethoxy)-1-(phenylmethyl)-2-pyridinecarboxylic acid, phenylmethyl ester and 0.54 g potassium hydroxyde were dissolved in 30 ml tetrahydrofuran and 3 ml H$_2$O. After stirring for 24 hours at room temperature, the THF was distilled off and 20 ml H$_2$O were added to the residue. The pH was adjusted to 3.5 with 2NHCl. Crystals of the title compound were formed and filtered off, washed with 20 ml H$_2$O and dried; yield 3 g of the title compound white crystals.
M.P. 155°-157° C.

EXAMPLE 9

(S)-[1-[[[[3-[[[3-Bromo-4,5-bis(phenylmethoxy)-2-pyridinyl]carbonyl]amino]-2-oxo-1-imidazolidinyl]sulfonyl]amino]carbonyl]-2-oxo-3-azetidinyl]carbamic acid, phenylmethyl ester 2.48 g of the title compound of Example 8, 0.92 g N-hydroxybenzotriazole and 1.24 g DCC were stirred in 50 ml THF at 0° C. for 345 minutes. The formed DCU was filtered off and washed with 10 ml THF. To the filtrate, was added a solution of 3.2 g [1-[[[(3-Amino-2-oxo-1-imidazolidinyl)-sulfonyl]amino]carbonyl]-2-oxo-3-azetidinyl]carbamic acid, phenylmethyl ester, trifluoroacetate (1:) salt and 5.6 ml MSTFA in 50 ml THF. After stirring overnight, the solvent was stripped off in vacuo and the oil residue was stirred with 100 ml ice water at pH 4.5 (2nHCl). A white solid of crude title compound, 4.71 g, H.I. 73%.
M.P.=112° C. (dec).

EXAMPLE 10

(S)-[1-[[[[3-[[[3-Bromo-4,5-bis(phenylmethoxy)-2-pyridinyl]carbonyl]amino]-2-oxo-1-imidazolidinyl]sulfonyl]amino]carbonyl]-2-oxo-3-azetidinyl]carbamic acid, phenylmethyl ester, monosodium salt 4.50 g of the title compound of Example 9 were dissolved in 50 ml $CH_3CN$ and a conc. solution of $NaHCO_3$ in water was added until the pH was 6.0. After a short time crystals of the title compound were formed. They were isolated by filtration after standing in the refrigerator for 1 hour. Yield: 2.84 g, H.I. 99%. M.P. 204° C. (dec.)

EXAMPLE 11

(S)-3-Amino-N-[[3-[[(3-bromo-1,4-dihydro-5-hydroxy-4-oxo-2-pyridinyl)carbonyl]amino]-2-oxo-1-imidazolidinyl-sulfonyl-2-oxo-1-azetidine carboxamide, trifluoroacetate salt 4.11 g of the title compound of Example 9 was dissolved in 50 ml TFA and 20 ml thioanisole and stirred for 16 hours at room temperature. Then 100 ml isopropanol were added. White crystals of title compound were obtained. 5.17 g.
M.P.=156° C. (dec.).

EXAMPLE 12

[3S(Z)[-2-[[[1-(2-Amino-4-thiazolyl)-2-[[1-[[[[-3-bromo-1,4-dihydro-5-hydroxy-4-oxo-2-pyridinyl)-carbonyl]amino]-2-oxo-1-imidazolidinyl]sulfonyl]-amino]-carbonyl]-2-oxo-3-azetidinyl]-amino]-2-oxoethylidene]amino]oxy]-2-methylpropanoic acid, disodium salt 1.28 g of the title compound of Example 11 and 2.4 ml MSTFA were dissolved in 25 ml $CH_3CN$ and stirred for 1 hour at room temperature. The solvent and the formed trifluoroacetic acid trimethylsilylester were then stripped off in vacuo at 30° C. The remaining oil was dissolved in 30 ml THF (dried). 1.2 g of name of (Z)-2-Amino-<a-[[2-(diphenylmethoxy)-1,1-dimethyl-2-oxoethoxylimino]-4-thiazoleacetic acid, 1H-benzotriazol-1-yl ester were added and the solution stirred for 3 hours at room temperature. After that time, the reaction was complete. The solvent was distilled off and the residue stirred for 1 hour with 50 ml ice water and two drops acetic acid. The formed solid was then filtered off, washed with water and dried to yield 2.41 g benzylhydryl ester of the title compound.

This material was stirred at 0° C. with 30 ml TFA/anisole for 45 minutes. After adding 200 ml ether a precipitate of the TFA-salt of the title compound was formed and isolated by filtration 1.35 g. This was suspended in 10 ml water and the pH was adjusted to 6.0 with $NaHCO_3$ forming a clear solution. MPLC on HP20 SS resin eluting with water yielded 0.8 g of title compound in fractions 18-24 (each 10 ml); light yellow solid.
M.P. 264°-268° C.

EXAMPLE 13

3-Bromo-2-(hydroxymethyl)-5-(phenylmethoxy)-4-(1H)-pyridonone 4.63 g of 5-(O-phenylmethyl) comenic acid were dissolved in 100 ml acetic acid; 1.65 g NaAc were added; and 3.2 g $Br_2$ were added dropwise while stirring at room temperature was continued. After stirring for 3 hours the solvent was distilled off and the residue stirred with 100 ml ice water. The title compound crystallized from the solution. It was isolated by filtration, washed with water and dried. Recrystallization from dioxane yielded 5.73 of the title compound. M.P.=214° C. (dec.)

EXAMPLE 14

3-Bromo-1,4-dihydro-4-oxo-5-(phenylmethoxy)-2-pyridinecarboxaldehyde 2.62 g of 1,4-dihydro-4-oxo-5-(phenylmethoxy)-2-pyridine carboxaldehyde and 0.83 g NaAc were dissolved in 50 ml AcOH and 2 g $Br_2$ were dropped in while stirring at room temperature. After 2 hours the solvent was distilled off and the residue stirred with 50 ml ice water. A precipitate of crude title compound was obtained. Isolation by filtration, washing with water and recrystallization from diozane yielded 2.61 g title compound.
M.P.=184° C. (dec.).

EXAMPLE 15

3-Bromo-1,4-dihydro-5-hydroxy-4-oxo-2-pyridine-carboxylic acid 3.24 g of the title compound of Example 8 were stirred in a mixture of 20 ml thioanisole and 30 ml TFA at room temperature for 16 hours. The solvents were distilled off in vacuo and the residue stirred with 50 ml ice water at pH 5.5 ($NaHCO_3$ were added). Solid title compound, beige crystals, were isolated by filtration after washing with water and drying over $P_2O_5$; yield: 2.2 g title compound. Title compound was also obtained by hydrogenation of the title compound of Example 8 in DMF, Pd/C (10%) as catalyst.
M.P.=189° C. (dec.).

What is claimed is:

1. Compound of the formula $$\begin{array}{c} R_1-NH \quad R^2 \; R_3 \\ \diagdown \quad | \; / \\ CH-C \\ | \quad | \\ C-N-C-NH-SO_2-R, \\ \diagup \quad \quad \| \\ O \quad \quad \quad O \end{array}$$

and pharmaceutically acceptable salts thereof, wherein R is

[structure: Hal-substituted pyridone connected via $A_1-N$ imidazolidinone ring $-N-A_2-CO-A_6-$ to hydroxypyridone with Hal and OH]

[structure: Hal-substituted pyridone connected via $A_1-N$ piperazinedione ring $-N-A_2-CO-A_6-$ to hydroxypyridone with Hal and OH]

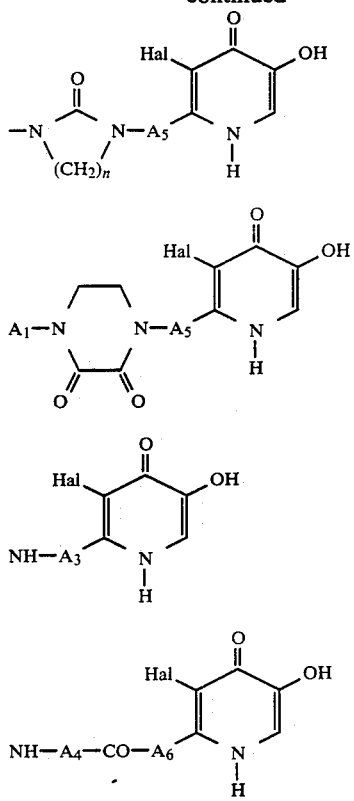

$R_1$ is an acyl group derived from a carboxylic acid;

$R_2$ and $R_3$ are the same or different and each is hydrogen, alkyl, alkenyl, alkynyl, cycloalkyl, phenyl, substituted phenyl or a 4, 5, 6 or 7-membered heterocycle or one of $R_2$ and $R_3$ is hydrogen and the other is azido, halomethyl, dihalomethyl, trihalomethyl, alkoxycarbonyl, 2-phenylethenyl, 2-phenylethynyl, carboxyl, —$CH_2X_1$ wherein $X_1$ is azido, amino, hydroxy, carboxyl, alkoxycarbonyl, alkanoylamino, phenylcarbonylamino, (substituted phenyl)-carbonylamino, alkylsulfonyloxy, phenylsulfonyloxy, (substituted phenyl)sulfonyloxy, phenyl, substituted phenyl, cyano,

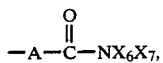

—S—$X_2$, or —O—$X_2$ (wherein A, $X_2$, $X_6$ and $X_7$ are as hereinafter defined); —S—$X_2$ or —O—$X_2$; wherein $X_2$ is alkyl, substituted alkyl, phenyl, substituted phenyl, phenylalkyl, (substituted phenyl)alkyl, alkanoyl, substituted alkanoyl, phenylalkanoyl, (substituted phenyl)alkanoyl, phenylcarbonyl, (substituted phenyl)carbonyl, or heteroarylcarbonyl; and in the case of when $X_1$ is O—$X_2$ then $X_2$ can also be alkylideneamino, alkanoylamino, carboxyalkylideneamino, alkylsulphonylamino, alkoxycarbonyl, alkylsulphonylamino or N,N-cyclodialkanoylamino,

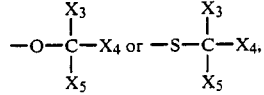

wherein one of $X_3$ and $X_4$ is hydrogen and the other is hydrogen or alkyl, or $X_3$ and $X_4$ when taken together with the carbon atom to which they are attached form a cycloalkyl group; and $X_5$ is formyl, alkanoyl, phenylcarbonyl, (substituted phenyl)-carbonyl, phenylalkylcarbonyl, (substituted phenyl)alkylcarbonyl, carboxyl, alkoxycarbonyl, aminocarbonyl, (substituted amino)-carbonyl, or cyano; or

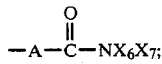

wherein A is CH=CH—, —$(CH_2)m$—, —$(CH_2)m$—O—, —$(CH_2)m$—NH—, or —$CH_2$—S—$CH_2$—, m is 0, 1 or 2, and $X_6$ and $X_7$ are the same or different and each is hydrogen, alkyl, phenyl or substituted phenyl, or $X_6$ is hydrogen and $X_7$ is amino, substituted amino, alkanoylamino or alkoxy, or $X_6$ and $X_7$ when taken together with the nitrogen atom to which they are attached form a 4, 5, 6 or 7-membered heterocycle;

$A_1$ is a single bond,

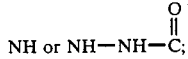

$A_2$ is a single bond,

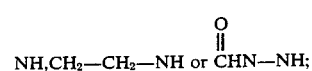

$A_3$ is a $(CH_2)p$—; NH—$CH_2$,

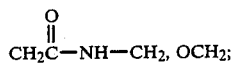

$A_4$ is —NH,
n is two or three;
p is zero or one;
q is zero or one;
t is one, two, three or four Hal is Br, Cl, or I $A_5$ is a single bond; $CH_2$; NH—$CH_2$; —N=CH—; —CO—NH—$(CH_2)q$ $A_6$ is a single bond; CH=CH; —$(CH_2)r$—;

wherein the term "substituted alkyl" refers to alkyl groups substituted with azio, amino, halogen, hydroxy, carboxy, cyano, alkoxycarbonyl, aminocarbonyl, alkanoyloxy, alkoxy, phenyloxy, (substituted phenyl)oxy, mercapto, alkylthio, phenylthio, (substituted phenyl)-thio, alkylsufinyl or alkylsulfonyl groups;

the term "substituted amino" refers to a group having the formula —$NX_8X_9$ wherein $X_8$ is hydrogen, alkyl, phenyl, substituted phenyl, phenylalkyl or (substituted phenyl)alkyl, and $X_9$ is alkyl, phenyl, substituted phenyl, phenylalkyl, (substituted phenyl)alkyl, hydroxy, cyano, alkoxy, phenylalkoxy or amino;

the term "heteroaryl" refers to pyridinyl, furanyl, pyrrolyl, thienyl, 1,2,3-triazolyl, 1,2,4-triazolyl, imdazolyl, thiazolyl, thiadiazolyl, pyrimidinyl, oxazolyl, triazinyl, tetrazol, tetrazolyl or one of the above groups substituted with one of more halogen, hydroxy, nitro, amino, cyano, trifluoromethyl, alkyl of 1 to 4 carbon atoms, alkoxy of 1 to 4 carbon atoms, alkylsulfonyl, phenyl, substituted phenyl, 2-furfurylideneamino, benzylideneamino, or substituted alkyl wherein the alkyl group has 1 to 4 carbon atoms, groups;

the term "a 4, 5, 6 or 7-membered heterocycle" refers to pyridinyl, furanyl, pyrrolyl, thienyl, 1,2,3-triazolyl, 1,2,4-triazolyl, imidazolyl, thiazolyl, thiadizolyl, pyrimidinyl, oxazolyl, triazinyl, tetrazolyl, azetinyl, oxetanyl, thietanyl, piperidinyl, piperazinyl, imidazolylidinyl, oxazolidinyl, pyrrolidinyl, tetrahydropyrimidinyl, dihydrothiazolyl or hexahydrazepinyl or one of the above groups substituted with one or more oxo, halogen, hydroxy, nitro, amino, cyano, trifluoromethyl, alkyl of 1 to 4 carbon atoms, alkoxy of 1 to 4 carbon atoms, alkylsulfonyl, phenyl, substituted phenyl, 2-furfurylideneamino, benzylideneamino, or substituted alkyl wherein the alkyl groups has 1 to 4 carbon atom, groups.

2. A compound according to claim 1 wherein $R_2$ and $R_3$ are the same or different and are hydrogen and methyl.

3. A compound according to claim 1 wherein

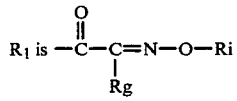

wherein Ri is selected from the group consisting of methyl, ethyl, trifluoromethyl,

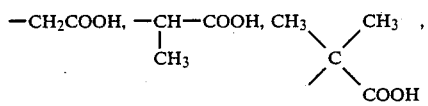

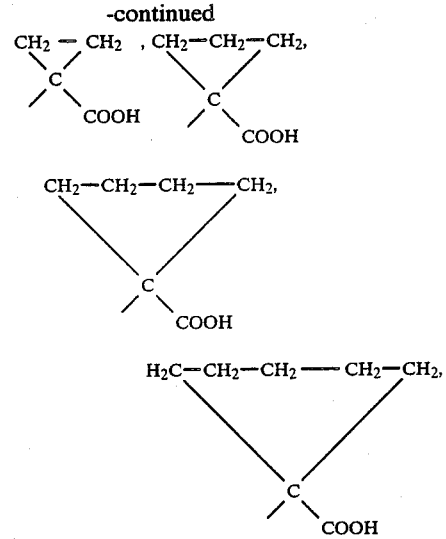

wherein Rg is 2-amino-4-thiazolyl.

4. A compound according to claim 1, (S)-[1-[[[[3-Bromo-1,4-dihydro-4-oxo-5-(phenylmethoxy)-2-pyridinyl]carbonyl]amino]-2-oxo-1-imidazolidinyl]sulfonyl]amino]carbonyl]-2-oxo-3-azetidinyl]carbamic acid, phenylmethyl ester.

5. A compound of claim 1, (S)-[1-[[[[3-Bromo-4,5-bis(phenylmethoxy)-2-pyridinyl]carbonyl]amino]-2-oxo-1-imidazolidinyl]-sulfonyl]amino]carbonyl]-2-oxo-3-azetidinyl]carbamic acid, phenylmethyl ester.

6. A compound according to claim 1, (S)-[1-[[[[3-Bromo-4,5-bis(phenylmethoxy)-2-pyridinyl]carbonyl]amino]-2-oxo-1-imidazolidinyl]-sulfonyl]amino]carbonyl]-2-oxo-3-azetidinyl]carbamic acid, phenylmethyl ester, monosodium salt.

7. A compound according to claim 1, (S)-3-Amino-N-[[3-[[(3-bromo-1,4-dihydro-5-hydroxy-4-oxo-2-pyridinyl)carbonyl]amino]-2-oxo-1-imidazolidinyl-sulfonyl-2-oxo-1-azetidine-carboxamide, trifluoroacetate salt.

8. A compound according to claim 1, [3S(Z)[-2-[[[-1-(2-Amino-4-thiazolyl)-2-[[1-[[[[-3-bromo-1,4--dihydro-5-hydroxy-4-oxo-2-pyridinyl)-carbonyl]-amino]-2-oxo-1-imidazolidinyl]sulfonyl]-amino]carbonyl]-2-oxo-3-azetidinyl]-amino]-2-oxoethylidene]amino]oxy]-2-methylpropanoic acid, disodium salt.

* * * * *